US008765680B2

(12) United States Patent
Ellis et al.

(10) Patent No.: US 8,765,680 B2
(45) Date of Patent: *Jul. 1, 2014

(54) METHOD FOR ADMINISTERING OMEGA-CONOPEPTIDE (71) Applicant: Jazz Pharmaceuticals International Limited, Hamilton (BM)

(72) Inventors: David J. Ellis, Los Altos, CA (US); George P. Miljanich, Redwood City, CA (US); David E. Shields, San Lorenzo, CA (US)

(73) Assignee: Jazz Pharmaceuticals International Limited, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/133,303

(22) Filed: Dec. 18, 2013

(65) Prior Publication Data
US 2014/0107038 A1   Apr. 17, 2014

Related U.S. Application Data

(60) Continuation of application No. 13/791,715, filed on Mar. 8, 2013, now Pat. No. 8,653,033, which is a continuation of application No. 13/616,607, filed on Sep. 14, 2012, now Pat. No. 8,513,198, which is a continuation of application No. 13/176,568, filed on Jul. 5, 2011, now Pat. No. 8,268,774, which is a continuation of application No. 12/898,516, filed on Oct. 5, 2010, now Pat. No. 7,977,307, which is a continuation of application No. 12/483,673, filed on Jun. 12, 2009, now Pat. No. 7,833,973, which is a continuation of application No. 11/831,702, filed on Jul. 31, 2007, now abandoned, which is a division of application No. 10/956,252, filed on Oct. 1, 2004, now Pat. No. 7,268,109.

(60) Provisional application No. 60/508,469, filed on Oct. 3, 2003, provisional application No. 60/508,625, filed on Oct. 2, 2003.

(51) Int. Cl.
| | | |
|---|---|---|
| A61K 38/00 | (2006.01) |
| A61K 38/16 | (2006.01) |
| C07K 14/00 | (2006.01) |
| A61K 31/445 | (2006.01) |
| A61K 38/17 | (2006.01) |
| A61K 47/18 | (2006.01) |
| A61K 47/12 | (2006.01) |
| A61K 31/485 | (2006.01) |
| A61K 31/4168 | (2006.01) |
| A61K 31/4468 | (2006.01) |
| A61K 31/451 | (2006.01) |
| A61K 31/4535 | (2006.01) |
| A61K 9/00 | (2006.01) |
| A61K 31/137 | (2006.01) |
| A61K 45/06 | (2006.01) |
| A61K 31/195 | (2006.01) |

(52) U.S. Cl.
CPC ............. *A61K 9/0085* (2013.01); *A61K 31/445* (2013.01); *A61K 38/17* (2013.01); *A61K 47/183* (2013.01); *A61K 47/12* (2013.01); *A61K 31/485* (2013.01); *A61K 31/4168* (2013.01); *A61K 31/4468* (2013.01); *A61K 31/451* (2013.01); *A61K 31/4535* (2013.01); *A61K 31/137* (2013.01); *A61K 45/06* (2013.01); *A61K 31/195* (2013.01); *A61K 38/1767* (2013.01)
USPC .......................... 514/18.3; 514/21.3; 530/324

(58) Field of Classification Search
CPC ............ A61K 2300/00; A61K 31/195; A61K 31/445; A61K 31/4468; A61K 38/17; C07K 7/00; C07K 7/06; C07K 7/08
USPC ................................. 514/18.3, 21.3; 530/324
See application file for complete search history.

(56) References Cited

U.S. PATENT DOCUMENTS

| 5,051,403 A | 9/1991 | Miljanich et al. |
| 5,189,020 A | 2/1993 | Miljanich et al. |

(Continued)

FOREIGN PATENT DOCUMENTS

| GB | 2196848 A | 5/1988 |
| WO | WO 93/13128 A1 | 7/1993 |

(Continued)

OTHER PUBLICATIONS

Anderson, et al.; "A Prospective Study of Long-Term Intrathecal Morphine in the Management of Chronic Nonmalignant Pain"; Neurosurgery; vol. 44, No. 2, pp. 289-301 (Feb. 1999).

(Continued)

*Primary Examiner* — Chih-Min Kam
(74) *Attorney, Agent, or Firm* — Perkins Coie LLP; Viola T. Kung (57) ABSTRACT

The present invention is directed to a method of producing analgesia in a mammalian subject. The method includes administering to the subject an omega conopeptide, preferably ziconotide, in combination with an analgesic selected from the group consisting of morphine, bupivacaine, clonidine, hydromorphone, baclofen, fentanyl 1, buprenorphine, and sufentanil, or its pharmaceutically acceptable salts thereof, wherein the ω-conopeptide retains its potency and is physically and chemically compatible with the analgesic compound. A preferred route of administration is intrathecal administration, particularly continuous intrathecal infusion. The present invention is also directed to a pharmaceutical formulation comprising an omega conopeptide, preferably ziconotide, an antioxidant, in combination with an analgesic selected from the group consisting of morphine, bupivacaine, clonidine, hydromorphone, baclofen, fentanyl, buprenorphine, and sufentanil.

24 Claims, 1 Drawing Sheet

(56) References Cited

U.S. PATENT DOCUMENTS

| | | | |
|---|---|---|---|
| 5,364,842 | A | 11/1994 | Justice et al. |
| 5,559,095 | A | 9/1996 | Miljanich et al. |
| 5,587,454 | A | 12/1996 | Justice et al. |
| 5,795,864 | A | 8/1998 | Amstutz et al. |
| 5,891,849 | A | 4/1999 | Amstutz et al. |
| 5,980,927 | A | 11/1999 | Nelson et al. |
| 6,054,429 | A | 4/2000 | Bowersox et al. |
| 6,136,786 | A | 10/2000 | Justice et al. |
| 6,379,882 | B1 | 4/2002 | Bitler et al. |
| 7,977,307 | B2 * | 7/2011 | Ellis et al. .................. 514/18.3 |
| 8,653,033 | B2 * | 2/2014 | Ellis et al. .................. 514/18.3 |

FOREIGN PATENT DOCUMENTS

| | | |
|---|---|---|
| WO | WO 97/01351 A1 | 1/1997 |
| WO | WO 01/76576 A2 | 10/2001 |
| WO | WO 01/83555 A2 | 11/2001 |
| WO | WO 03/078408 A1 | 9/2003 |
| WO | WO 2005/032556 A1 | 3/2005 |

OTHER PUBLICATIONS

Atanassoff, et al.; "Ziconotide, A New N-Type Calcium Channel Blocker, Administered Intrathecally for Acute Postoperative Pain"; Regional Anesthesia and Pain Medicine; vol. 25, No. 3, pp. 274-278 (May-Jun. 2000).

Basilico, et al.; "Influence of w-Conotixin on Morphine Analgesia and Withdrawal Syndrome in Rats"; European Journal of Pharmacology; vol. 218 (1992) pp. 75-81.

Bennett, et al.; "Evidence-Based Review of the Literature on Intrathecal Delivery of Pain Medication"; Journal of Pain and Symptom Management; vol. 2, No. 2 (Aug. 2, 2000) pp. S12-S36.

Brose, et al.; "Use of Intrathecal SNX-111, a Novel, N-type, Voltage-Sensitive, Calcium Channel Blocker, in the Management of Intractable Brachial Plexus Avulsion Pain"; The Clinical Journal of Pain; vol. 13, pp. 256-259 (1997).

Coffey, et al.; "Inflammatory Mass Lesions Associated with Intrathecal Drug Infusion Catheters: Report and Observations on 41 Patents"; Neurosurgery; vol. 50, No. 1 (Jan. 2002) pp. 78-87.

Follett, et al.; "Intrathecal Analgesia and Catheter-tip Inflammatory Masses"; Anesthesiology; vol. 99, No. 1 (Jul. 2003) pp. 5-6.

Gatscher, S. et al; "Combined Intrathecal Baclofen and Morphine Infusion for the Treatment of Spasticity Related Pain and Central Deafferentiation Pain"; Acta Neurochir Suppl.; vol. 79 (2002) pp. 75-76.

Gradert, et al.; "Safety of Chronic Intrathecal Morphine Infusion in a Sheep Model"; Anesthesiology; vol. 99, No. 1 (Jul. 2003) pp. 188-198.

Hassenbusch, et al.; "Current Practices in Intraspinal Therapy—A Survey of Clinical Trends and Decision Making"; Journal of Pain and Symptom Management; vol. 20, No. 2 (Aug. 2000) pp. S4-S11.

Hassenbusch, et al.; "Polyanalgesic Consensus Conference 2003: An Update on the Management of Pain by Intraspinal Drug Delivery—Report of an Expert Panel"; Journal of Pain and Symptom Management; vol. 27, No. 6 (Jun. 2004) pp. 540-563.

Horvath, et al.; "Role of Calcium Channels in the Spinal Transmission of Nociceptive Informatin From the Mesentery"; International Study of Pain; vol. 93 (2001) pp. 35-41.

Krames, et al.; "Intrathecal Infusional Analgesia for Nonmalignant Pain; Analgesic Effecacy of Intrathecal Opioid With or Without Bupivacaine", Journal of Pain and Symptom Management; vol. 8, No. 8 (Nov. 1993) pp. 539-548.

Likar, et al.; "Long-term Intraspinal Infusions of Opioids with a New Implantable Medication Pump"; Arzneim.-Forsch./Drug Res. 49; vol. I, No. 6, pp. 489-493 (1999).

McMillan, et al.; "Catheter-Associated Masses in Patients Receiving Intrathecal Analgesic Theraphy"; Anesthesia Analogy; vol. 96 (2003) pp. 186-190.

Presley, et al.; "Chronic, Opioid-Resistant, Neuropathic Pain: Marked Analgesic Efficacy of Intrathecal Ziconotide"; Am. Pain Soc. Abstr; vol. 17, p. 697 (1998).

Smith, et al.; "Influence of Voltage-Sensitive CA++Channel Drugs on Bupivacaine Infiltration Anesthesia in Mice; Anesthesiology "; vol. 95 (2001) pp. 1189-1197.

Wang, et al.; "Ziconotide Chemistry and Blockade of N-Type VSCCS"; CNS Drug Review; vol. 6, No. 1 (2000) pp. 2-20.

Wang, Y.X. et al.; "Interactions of Intrathecally Administrered Ziconotide, a Selective Blocker of Neuronal N-Type Voltage-Sensitive Calcium Channels, with Morphine on Nociception in Rats"; Pain; vol. 84, No. 2-3 (2000) pp. 271-281.

Wei, et al.; "Spinal Morphine/Clonidine Antinociceptive Synergism; Involvement of G Proteins and N-Type Voltage-Dependent Calcium Channels"; The Journal of Pharmacology and Experimental Therapeutics; vol. 278, No. 3 (1996) pp. 1392-1407.

Yaksh, et al.; "Chronically Infused Intrathecal Morphine in Dogs"; Anesthesiology; vol. 99 (2003) pp. 174-187.

Yong-Xiang Wang, et al.; "Analgesic Properties of Ziconotide, a Selective Blocker of N-Type Neuronal Calcium Channels"; CNS Drug Reviews; vol. 6, No. 1 (2000) pp. 1-20.

* cited by examiner

METHOD FOR ADMINISTERING OMEGA-CONOPEPTIDE

This application is a continuation of U.S. application Ser. No. 13/791,715, filed Mar. 8, 2013, now U.S. Pat. No. 8,653,033; which is a continuation of U.S. application Ser. No. 13/616,607, filed Sep. 14, 2012, now U.S. Pat. No. 8,513,198; which is a continuation application of U.S. application Ser. No. 13/176,568, filed Jul. 5, 2011, now U.S. Pat. No. 8,268,774; which is a continuation application of U.S. application Ser. No. 12/898,516, filed Oct. 5, 2010, now U.S. Pat. No. 7,977,307; which is a continuation application of U.S. application Ser. No. 12/483,673, filed Jun. 12, 2009, now U.S. Pat. No. 7,833,973; which is a continuation of U.S. application Ser. No. 11/831,702, filed Jul. 31, 2007, now abandoned; which is a divisional application of U.S. application Ser. No. 10/956,252, filed Oct. 1, 2004, now U.S. Pat. No. 7,268,109; which claims the benefit of U.S. Provisional Application Nos. 60/508,625, filed Oct. 2, 2003, and 60/508,469, filed Oct. 3, 2003; the above-identified applications are incorporated herein by reference in their entirety.

FIELD OF THE INVENTION

The present invention relates to a method of providing analgesia for nociceptive and neuropathic pain by using a ω-conopeptide, such as ziconotide, in combination with another pain drug.

BACKGROUND OF THE INVENTION

In general, although brain pathways governing the perception of pain are still not completely understood, sensory afferent synaptic connections to the spinal cord, termed "nociceptive pathways" have been documented in some detail. In the first part of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region (μgeer, P. L., Eccles, J. C., and μgeer, E. G. (1987). Molecular Neurobiology of the Mammalian Brain, Plenum Press, New York). Analgesia, or the reduction of pain perception, can be effected directly by decreasing transmission along such nociceptive pathways. Analgesic opiates are thought to act by mimicking the effects of endorphin or enkephalin peptide-containing neurons, which synapse at the C- or A-fiber terminal and inhibit release of neurotransmitters, including substance P. Descending pathways from the brain are also inhibitory on C- and A-fiber firing.

Neuropathic pain is a particular type of chronic pain that has a complex and variable etiology. It is frequently a chronic condition attributable to complete or partial transection of a nerve, trauma or injury to a nerve, nerve plexus or soft tissue, or other conditions, including cancer, AIDS and idiopathic causes. Neuropathic pain is characterized by hyperalgesia (lowered pain threshold and enhanced pain perception) and by allodynia (pain from innocuous mechanical or thermal stimuli). The condition is progressive in nature. Because the hyperesthetic component of neuropathic pain does not respond to the same pharmaceutical interventions as does more generalized and acute forms of pain, development of effective long-term treatment modalities has been problematic.

Opioid compounds (opiates) such as morphine, while effective in producing analgesia for many types of pain, are not always effective, and may induce tolerance in patients. When a subject is tolerant to opioid narcotics, increased doses are required to achieve a satisfactory analgesic effect. At high doses, these compounds produce side effects, such as respiratory depression, which can be life threatening. In addition, opioids frequently produce physical dependence in patients. Dependence appears to be related to the dose of opioid taken and the period of time over which the drug is taken by the subject. For this reason, alternate therapies for the management of chronic pain are widely sought after. Compounds that serve as either a replacement for or as an adjunct to opioid treatment in order to decrease the dosage of analgesic compound required, have utility in the treatment of pain, particularly pain of the chronic, intractable type.

Although various types of calcium blocking agents, including a number of L-type calcium channel antagonists and calcium chelators, have been tested as adjunct therapy to morphine analgesia, positive results are attributed to direct effects on calcium availability, since calcium itself is known to attenuate the analgesic effects of certain opioid compounds (Ben-Sreti). EGTA, a calcium chelating agent, is effective in increasing the analgesic effects of opioids. However, results from tests of calcium antagonists as adjunct therapy to opioids have been contradictory. Some L-type calcium channel antagonists have been shown to increase the effects of opioids, while others of these compounds have been shown to decrease opioid effects (Contreras).

It is known to use omega-conopeptide to treat pain. For example, U.S. Pat. No. 5,051,403 describes the use of omega-conopeptides having defined binding/inhibitory properties in the treatment of ischemia-related neuronal damage. U.S. Pat. No. 5,364,842 demonstrates the effectiveness of omega-conopeptide compositions in certain animal models of pain. Specifically, omega-conopeptides MVIIA and TVIA and derivatives thereof having related inhibitory and binding activities were demonstrated to produce analgesia in animal models of analgesia in which morphine is the standard positive control. PCT/US92/11349 discloses that such conopeptides also produce relief from neuropathic pain, where morphine is not expected to produce positive results. U.S. Pat. No. 5,891,849 describes that omega-conopeptides are effective in preventing progression of neuropathic pain.

U.S. Pat. No. 6,136,786 is directed to a method of enhancing the analgesic effect produced by an opiate in a mammalian subject, comprising administering to the subject an effective dose of an omega-conopeptide having activity to (a) inhibit electrically stimulated contraction of the guinea pig ileum, and (b) bind to omega-conopeptide MVIIA binding sites present in neuronal tissue.

Wang and Bowersox (CNS Drug Reviews, 6(1): 2-20, (2000)) have reported the administration of ziconotide by intrathecal bolus injection with morphine, clonidine, baclofen, bupivacaine in rats. Intrathecal bolus injections of a combination of ziconotide and morphine dose-dependently suppress formalin-induced tonic flinch responses in rats. Intrathecal bolus injections of clonidine and ziconotide administered in combination dose-dependently suppress tonic pain behavior in the rat hindpaw formalin test. Administration of ziconotide and baclofen in combination by intrathecal bolus injection produces additive analgesia in the rat hindpaw formalin test. When co-administered with ziconotide by intrathecal bolus injection, bupivacaine (a sodium channel blocker) does not significantly alter ziconotide-induced analgesia in the formalin test.

Wang, et al. (Pain, 84: 271-281 (2000)) disclose that intrathecal injections of ziconotide and morphine in rats (1 μg morphine+0.1 μg ziconotide and 3 μg morphine+0.3 μg ziconotide) blocked acute phase flinch responses following subcutaneous injection of formalin, which were significantly different from controls that received intrathecal bolus injection of 100 saline. The reference also discloses that concurrent infusion of intrathecal ziconotide (0.03 μg/hr) with morphine (15 μg/hr) for 7 days in rats produced marked antinociceptive responses to noxious heat stimuli as measured by the hot-plate test or tail immersion test during the first day of infusion. Thermal nociceptive thresholds thereafter declined toward the control level.

There is a need for an improved method of reducing pain in a human subject. The improved method reduces the side effects of pain drugs, the necessary doses of each drug, or the drug interactions.

SUMMARY OF THE INVENTION

The present invention is directed to a pharmaceutical formulation comprising an ω-conopeptide and an analgesic compound selected from the group consisting of morphine, bupivacaine, clonidine, hydromorphone, baclofen, fentanyl citrate, buprenorphine, and sufentanil citrate, or its pharmaceutically acceptable salts thereof, wherein the ω-conopeptide retains its potency and is physically and chemically compatible with the analgesic compound. A preferred ω-conopeptide is ziconotide. The pharmaceutical formulation is suitable for intrathecal administration.

The present invention also provides a method for reducing pain. The method comprises the steps of administering to a subject an omega conopeptide, preferably ziconotide, in combination with an analgesic compound selected from the group consisting of morphine, bupivacaine, clonidine, hydromorphone, baclofen, fentanyl citrate, buprenorphine, and sufentanil citrate, or its pharmaceutically acceptable salts thereof, wherein the ω-conopeptide retains its potency and is physically and chemically compatible with the analgesic compound. A preferred route of administration is intrathecal administration, particularly continuous intrathecal infusion.

DETAILED DESCRIPTION OF THE INVENTION

The present invention is directed to a method of combination drug therapy in which a patient is administered with a ω-conopeptide and one or more other analgesic drugs. The ω-conopeptide and the other analgesic drugs are co-administered by any of a number of routes of administration, particularly by intrathecal administration, and especially by continuous intrathecal administration. This invention fulfills a need for a method of dispensing analgesic drugs in combination with a ω-conopeptide so as to reduce the necessary doses of each drug in the combination, and so as to reduce the side effects concomitant to each analgesic. The combination administration of analgesic drugs with a ω-conopeptide also provides an additive, or even synergistic effect in reducing pain in a subject.

The present invention provides a treatment method for reducing neuropathic pain in a human patient. The present invention is also useful in treating chronic pain such as that associated with cancer or AIDS. The method comprises administering to a subject an effective amount of an omega conopeptide, preferably ziconotide, combined with one or more traditional analgesic compounds such as opioids, local anesthetics, adrenergic agonists, glutamate receptor antagonists, NMDA antagonists, and other analgesic agents.

Opioids suitable for the present invention include morphine, hydromorphone, fentanyl, fentanyl citrate, sufentanil, sufentanil citrate, methadone, buprenorphine, and meperidine. Local anesthetics include bupivacaine, ropivacaine, and tetracaine. Adrenergic agonists include clonidine and tizanidine. Glutamate receptor antagonists include dextrorphan, dextromethorphan, and memantine. NMDA antagonists include ketamine. Other analgesic agents include adenosine, aspirin, baclofen, droperidol, gabapentin, ketorolac, midazolam, neostigmine, octreotide (a somatostatin analogue), midazolam (a sedative/hypnotic) and valproate (an anti-epileptic).

Omega Conopeptides

Omega conopeptides, also known as omega conotoxins, are a group of small (24-29 amino acids), disulfide-rich polypeptides, found in the venoms of predatory marine snails that belong to the genes *Conus*. All ω-conopeptides bind to N-type voltage sensitive calcium channels (VSCC), which are found exclusively in neurons, although the binding affinities for specific VSCC subtypes may differ. In response to nerve cell membrane depolarization, N-type VSCCs open and permit calcium entry that results in neurotransmitter release. N-type VSCCs are abundant in the Rexed laminae I and II of the dorsal horn of the spinal cord, where primary afferent fibers in the pain signaling synapse for the first time. Omega conopeptides bind to N-type VSCCs in the Rexed laminae I and II and blocks calcium transport into the presynaptic terminal, thereby blocking neurotransmitter release. By blocking calcium entry at N-type VSCCs in this location, pain signals, including those that develop after peripheral nerve injury and characterize peripheral neuropathies, are less easily transmitted or are blocked completely.

A preferred omega conopeptide useful for this invention is ziconotide, which is available commercially as PRIALT™. Ziconotide (SNX-111), a 25-amino acid peptide, is a synthetic version of a naturally-occurring peptide found in the venom of the marine snail *Conus magus*. Ziconotide specifically and selectively binds to VSCCs.

Omega-Conopeptides and Treatment of Chronic and Neuropathic Pain

Treatment with omega conopeptides, preferably ziconotide, is useful in preventing progression of neuropathic pain. Analgesic omega-conopeptides are effective as analgesic agents both in traditional opiate-sensitive models of nociceptive pain, such as the Rat Tail-Flick model or the rat formalin model, as well as in opiate-resistant models of pain, such as allodynia model of neuropathic pain.

Ziconotide has a unique combination of pharmacological actions. Specifically, intrathecally-administered ziconotide is more potent, longer acting, and more specific in its actions than are traditional neuropathic pain targeting drugs such as morphine or clonidine.

Ziconotide are effective with intrathecal administration in animal models of acute, chronic, and neuropathic pain. Ziconotide, unlike morphine, does not suppress respiratory function and does not have addiction potential. Once a therapeutic dose is reached, tolerance does not appear to develop as it does with opioids. Ziconotide are effective in both non-neuropathic (visceral, somatic) and neuropathic cancer pain and in non-malignant neuropathic pain states.

Stability of Ziconotide

Dilute solutions of omega-conopeptides are generally unstable in solution, as evidenced by oxidation of methionine residues and reduction or loss of biological activity. In particular, ziconotide, which contains a methionine at position 12, is approximately 10-fold less potent in binding to omega-conopeptide MVIIA binding sites when its methionine is present in the sulfoxy form. Omega-conopeptides can, however, be significantly stabilized in solution by preventing oxidation of methionine residues present in the peptide structure. Ziconotide oxidation, for example, can be prevented by addition of lactate buffer to the composition. More particularly, buffers containing 150 mM lactate buffer, pH 4-4.5 improve stability of the compound considerably. Solutions of ziconotide in which the peptide concentration is less than about 0.1 mg/ml oxidize rapidly when dissolved in water, saline, or any of a number of buffers used in the art of peptide chemistry. Solutions of ziconotide ranging from 0.01-0.1 mg/ml are stable at 45° C. for weeks when stabilized with lactate (150 mM, ph 4-4.5). Buffers containing 50 µg/ml methionine are also effective in stabilizing ziconotide when either 150 mM lactate buffer or acidified saline (pH 4-4.5) is used to buffer the solution.

Advantages of Combination Therapy with Omega Conopeptides and Other Analgesic Compounds Combination therapy of omega conopeptides with other analgesic compounds offers several advantages over single drug administrations. First, administration of a combination drug therapy may allow dose reduction of the individual drug components, which reduces development of drug tolerance to either or both drugs, and reduces the likelihood of drug interactions. The reduced concentration of each drug also limits the dose dependent side effects of the drugs. In addition, the effective dose (ED50) is reduced because a lower concentration of each drug is needed to achieve therapeutic effect.

Second, the administration of a combination of two drugs, which utilize different mechanisms to interrupt intractable or chronic pain mechanisms, magnifies the beneficial effects of either or both drugs in an additive or synergistic fashion.

Third, intrathecal administration of ziconotide in combination with another drug decreases or eliminates the usual sequelae of chronic intrathecal catheterization with morphine such as granuloma formation at the catheter tip.

However, not all drugs are compatible in terms of stability and activity. Ziconotide, when stored at µg/mL concentration, is particularly subjected to interaction with other drugs in the admixture. For continuous intrathecal infusion, the admixture of drugs is stored at 37° C. over a period of one week to a month or longer, it is important that ziconotide retains its activity over 80%, preferably over 90% during storage and administration.

Other Analgesic Compounds

Morphine

Morphine (7,8-didehydro-4,5-epoxy-17-methylmorphinan-3,6-diol) is an opium alkaloid that has potent analgesic properties toward all types of pain. Morphine readily causes addiction, and is therefore a drug of last resort when other pain-relieving drugs prove to be inadequate. INFUMORPH® (morphine sulfate) is a fairly stable salt prepared by neutralizing morphine with dilute sulfuric acid. Morphine sulfate does lose water of hydration and darkens on exposure to air and light. This morphine salt is especially used in England by oral administration for the management of pain in cancer patients. Typical intrathecal doses of morphine alone range between 0.5 and 75 mg/day, and usually between 2 and 20 mg/day.

Hydromorphone

DILAUDID® (Hydromorphone Hydrochloride; dihydromorphinone hydrochloride) is a synthetic derivative of morphine prepared by the catalytic hydrogenation and dehydrogenation of morphine under acidic conditions using a large excess of platinum or palladium. Hydromorphone is a substitute for morphine (5 times as potent) but has approximately equal addicting properties and a shorter duration of action. One advantage of hydromorphone over morphine is that it gives less daytime sedation or drowsiness. Typical daily dosages of hydromorphone range between 0.05 and 15 mg/day.

Bupivacaine

MARCAINE® (Bupivacaine hydrocholoride) is a sodium channel blocker that is used clinically both as a primary local anesthetic agent and as an adjuvant spinal analgesic. Bupivacaine is a local anesthetic of the amide class similar in chemical structure and properties to meprivacaine. The duration of action of bupivacaine is 2 to 3 times longer than that of tetracaine. The potency of bupivacaine is comparable to tetracaine, but both are about 4 times that of meprivacaine and lidocaine. Typical intrathecal dosages of bupivacaine alone range between 1 and 100 mg/day, usually between 5 and 15 mg/day.

Ropivacaine

Ropivacaine is an amide-type local anesthetic with a relative affinity for A-delta and C fibers over A-beta fibers that makes it a choice for analgesia without motor loss. Ropivacaine has less affinity for motor blockade with effective sensory blockade when compared to bupivacaine, and lower lipid solubility than buipvacaine. Compared to bupivacaine, ropivacaine is less toxic, more selective for sensory versus motor nerves between the sensory and motor blockage, and has lower solubility resulting in greater spinal segmental spread. Compared to bupivacaine, ropivacaine has a shorter duration of action and biphasic time-dependent pharmacokinetics. (G. Bennett et al. (2000), Evidence-Based Review of the Literature on Intrathecal Delivery of Pain Medication, Journal of Pain and Symptom Management, 20: S12-S11).

Clonidine

DURACLON (Hydromorphone; 2,6-dichloro-N-2-imidazolidinylidenebenzenamine) is an antagonist at $\alpha_2$ adrenergic receptors, $P_1$ purinergic receptors, and $H_2$ histamine receptors. Clonidine is used as a central antihypertensive drug and also abolishes most symptoms of opiate withdrawal. Clonidine is used clinically to treat both acute (postoperative) pain and chronic pain syndromes. Known side effects of clonidine when used clinically for the management of pain include hypotension and bradycardia. Typical daily intrathecal dosages of clonidine alone range between 10 and 400 µg, usually between 25 and 75 µg/day.

Baclofen

Baclofen (γ-amino-β-(p-chlorophenyl) butyric acid) is a 4-chlorophenyl derivative of γ-aminobutyric acid (GABA) that acts as a selective agonist for the $GABA_B$ receptor and inhibits the release of other neurotransmitters in the central nervous system. Baclofen is used for its antispastic (muscle-relaxing) effects, and is especially indicated for intractable spasticity caused by spinal cord injury or multiple sclerosis. Baclofen also possess analgesic properties and is antinociceptive when administered parenterally or intrathecally in rats. The typical dosage range of baclofen alone for intrathecal administration is 20-2000 µg/day, and usually 300-800 µg/day.

Fentanyl Citrate

SUBLIMAZE® (Fentanyl citrate; (N-(1-phenethyl-4-piperidyl)propionanilide citrate) is an anilide derivative with analgesic activity 50 times that of morphine in man. Fentanyl Citrate is use primarily as an adjunct to anaesthesia, and has a rapid onset (4 minutes) and a short duration of action. Side effects similar to those of other potent analgesics are common-in particular, respiratory depression and bradycardia. Fentanyl citrate has dependence liability. Fentanyl is typically administered intrathecally at a dose of 10 μg/hour.

Sufentanil Citrate

Sufentanil citrate (N-[4-(methoxymethy)-1-[2-(2-thienyl)ethyl]-4-piperidinyl]-N-phenylpropanamide 2-hydroxy-1,2,3-propanetricarboxylate) is a potent opioid analgesic. Sufentanyl is typically administered intrathecally at doses ranging from 0.1 to 1.5 μg/hour.

Pharmaceutical Formulation

Formulations that comprise omega-conopeptides at various concentrations in combination with any one or more of several drugs at various concentrations are envisioned, including but not limited to morphine, methadone, hydromorphone, buprenorphine, meperidine, fentanyl (e.g. fentanyl citrate), sufentanil (e.g. sufentanil citrate), bupivacaine, ropivacaine, tetracaine, clonidine, tizanidine, dextrorphan, dextromethorphan, memantine, ketamine, octreotide, valpreotide, baclofen, midazolam, neostigmine, aspirin, adenosine, gabapentin, ketorolac, octreotide, or droperidol, (or a pharmaceutically acceptable salt thereof), wherein ziconotide retains its potency and is physically and chemically compatible with the analgesic compound.

The present invention is directed to a pharmaceutical formulation comprising an ω-conopeptide and an analgesic compound selected from the group consisting of morphine, bupivacaine, clonidine, hydromorphone, baclofen, fentanil citrate, buprenorphine, and sufentanyl citrate, or its pharmaceutically acceptable salts thereof, wherein the ω-conopeptide retains its potency and is physically and chemically compatible with the analgesic compound. A preferred ω-conopeptide is ziconotide. The pharmaceutical formulation optionally comprises a pharmaceutically acceptable carrier.

The pharmaceutical formulation of the present invention is suitable for intrathecal administration, particularly continuous intrathecal infusion. A preferred formulation is stable in a drug dispensing implantable pump at 37° C. for at least 7 days.

Method for Reducing Pain

The present invention provides a method for reducing pain in a patient. The method comprises administering to a patient an effective amount of an ω-conopeptide and an effective amount of an analgesic compound, wherein the ω-conopeptide and the analgesic compound are compatible and retain both activity during the administration. The ω-conopeptide and the analgesic compound can each be in a separate formulation and be co-administered simultaneously or sequentially. Alternatively, the ω-conopeptide and the analgesic compound can be pre-mixed and form one formulation for administration.

The pharmaceutical formulation can be administered in a variety of ways, including but not limited to regionally or systemically, orally, parenterally, subcutaneously, intraperitoneally, intravascularly, perineurally, epidurally, and most particularly, intrathecally. Intrathecal delivery of drugs can be done by either a bolus injection or a continuous infusion. A bolus injection is defined as the injection of a drug (or drugs) in a high quantity (called a bolus) at once, the opposite of gradual administration (as in intravenous infusion). Continuous infusion is defined as the administration of a drug or drug combination over a prolonged period of time. The formulations may be formulated in a variety of ways, depending upon the manner of introduction. The dose of each drug in the drug formulation depends upon the route of administration. Generally, dosages and routes of administration of the compounds are determined according to the site of the pain and the size of the subject, according to standard pharmaceutical practices.

A therapeutically effective dose is an amount effective to produce a significant reduction in the chronic or neuropathic pain. The dose levels can sometimes be estimated, for new compounds, by comparison with established effective doses of known compounds with structural similarities, taking into consideration predicted variations in bioavailability, biodistribution, and other pharmacokinetic properties, as can be empirically determined by persons skilled in the art. It is contemplated that dosages of drugs used in combination drug therapy are the same or lesser concentration than the concentration of each drug when administered alone by the same route of administration.

The combined drug formulation can be administered at any times after the onset of the neuropathic pain, or before an event known to elicit conditions of chronic or neuropathic pain.

In one embodiment of the invention, the method for reducing pain comprises the steps of administering to a patient an effective amount of an ω-conopeptide and an effective amount of an analgesic compound selected from the group consisting of hydromorphone, buprenorphine, fentanyl, and sufentanil, or its pharmaceutically acceptable salts thereof. A preferred ω-conopeptide is ziconotide. A preferred route of administration is intrathecal administration, particularly continuous intrathecal infusion. The ω-conopeptide and the analgesic compound can each be in a separate formulation and be co-administered simultaneously or sequentially. Alternatively, the ω-conopeptide and the analgesic compound can be pre-mixed and form one formulation for administration.

In another embodiment of the invention, the method for reducing pain comprises the steps of administering to a patient an effective amount of an ω-conopeptide and an effective amount of an analgesic compound selected from the group consisting of bupivacaine, clonidine, and baclofen, or its pharmaceutically acceptable salts thereof, wherein said administering is continuous intrathecal infusion. A preferred ω-conopeptide is ziconotide. The ω-conopeptide and the analgesic compound can each be in a separate formulation and be co-administered simultaneously or sequentially. Alternatively, the ω-conopeptide and the analgesic compound can be pre-mixed and form one formulation for administration.

In yet another embodiment of the invention, the method for reducing pain comprises the steps of administering to a patient intrathecally a pharmaceutical formulation comprising a ω-conopeptide and morphine, or its pharmaceutically acceptable salts thereof. A preferred ω-conopeptide is ziconotide. A preferred route of administration is continuous intrathecal infusion.

The present invention is also directed to a method for reducing pain in a patient susceptible to intrathecal opiod-induced granuloma formation. The method comprises intrathecally administering to the patient an omega conopeptide. The method optionally further comprises administering to the patient via continuous intrathecal infusion an effective amount of an analgesic compound selected from the group consisting of bupivacaine, clonidine, and baclofen, or its pharmaceutically acceptable salts thereof.

The invention is illustrated further by the following examples that are not to be construed as limiting the invention in scope to the specific procedures described in it.

EXAMPLES

Example 1

Stability of Ziconotide

Objectives:

Ziconotide drug product is currently formulated at 100 μg/mL in saline, pH adjusted to 4.3. Free methionine (50 μg/mL) is added to the solution as an antioxidant. This solution has demonstrated excellent stability when stored at 2-8° C. for three years. When this material is used in clinical trials, physicians frequently dilute the drug product to 25 μg/mL, using silane. This reduces the concentration of free methionine four-fold, and subjects the peptide to additional oxidative degradation. The objective of this study is to investigate the stability of a 25 μg/mL Ziconotide solution in 50 μg/mL methionine.

To investigate the feasibility of manufacturing a 25 μg/ml ziconotide in 50 μg/ml methionine, stability profiles of 25 μg/ml were generated from an accelerated stability study at 25° C., 40° C., and 60° C. at pre-determined time points.

To prepare 25 μg/ml ziconotide solution, dilutions were performed in a glove box attached to a nitrogen gas source to ensure an oxidative-free environment. 255 ml of L-methionine/sodium chloride solution (50 μg/ml L-methionine) was measured and transferred to 500 ml storage bottles. 85 ml of ziconotide REF007 (100 μg/ml) was added to the storage bottle, which was then closed tightly and stirred for a minimum of 5 minutes, after which pH was determined. If pH was outside the range of 4.25 to 4.35, pH was adjusted with the addition of 0.15N NaOH or 0.15N HCl to bring it within the range. The solution was then aliquoted at 20 ml per vial. Vials were capped with rubber stoppers and an aluminum seal. Vials were stored at 5° C., 25° C., 40° C., or 60° C.

The stability of the ziconotide formulation was analyzed for percent label claim at 4 temperatures (5° C., 25° C., 40° C., or 60° C.), and was tested in fresh vials at each temperature at day 0, 1 month, 2 months, and 3 months post dilution. At each test, appearance and pH were assessed. In addition, RP-HPLC was used to identify, concentrate, and purify each sample. Arrhenius analysis (assuming linearity) was conducted to estimate stability as a function of time at 5° C. Through the Arrhenius Plot Analysis, the ziconotide formulation (25 μg/ml) is estimated to meet label requirements (>90%) for approximately 4442 months (approximately 370 years).

Example 2

Compatibility of Ziconotide with Other Intrathecal Drugs Physical Compatibility

The physical compatibility of the ziconotide with 7 other currently marketed intrathecal drugs (Hydromorphone HCL, Bupivacaine HCL, Morphine Sulfate Injection, Fentanyl Citrate Injection, sufentanil citrate, Baclofen for Injection, and Clonidine HCL for Injection) was determined by evaluating appearance, color, pH, and particulate matter before mixing and 24 hours after mixing in admixture. In order to be considered physically compatible, admixture solutions must have met the USP criteria for particulates, must remain within acceptable pH, and must have no changes in color or appearance.

100 μg of Ziconotide was mixed with each drug in a 1:8 and a 8:1 ziconotide to drug volume ratio. Data from this study is listed in Table 1 below:

TABLE 1

Physical Compatibility

| Ziconotide Admixture | Ratio Ziconotide:Second Drug | Physical Compatibility |
| --- | --- | --- |
| Hydromorphone HCl, 2 mg/mL (Dilaudid HP) | 1:8 | Yes |
| Hydromorphone HCl, 2 mg/mL (Dilaudid HP) | 8:1 | Yes |
| Bupivacaine HCl, 7.5 mg/mL (Marcaine Spinal) | 1:8 | Yes |
| Bupivacaine HCl, 7.5 mg/mL (Marcaine Spinal) | 8:1 | Yes |
| Morphine sulfate, 25 mg/mL (Infumorph 500) | 1:8 | Yes |
| Morphine sulfate, 25 mg/mL (Infumorph 500) | 8:1 | Yes |
| Morphine Sulfate Injection, 1 mg/mL | 1:8 | Yes |
| Morphine Sulfate Injection, 1 mg/mL | 8:1 | Yes |
| Fentanyl Citrate Injection, USP 0.05 mg/mL | 1:8 | Yes |
| Fentanyl Citrate Injection, USP 0.05 mg/mL | 8:1 | Yes |
| Sufenta Injection 0.05 mg/mL (Sufentanil citrate) | 1:8 | Yes |
| Sufenta Injection 0.05 mg/mL (Sufentanil citrate) | 8:1 | Yes |
| Sufentanil Citrate Injection 0.05 mg/mL | 1:8 | Yes |
| Sufentanil Citrate Injection 0.05 mg/mL | 8:1 | Yes |
| Baclofen for Injection, 2 mg/mL (Lioresal Intrathecal) | 1:8 | Yes |
| Baclofen for Injection, 2 mg/mL (Lioresal Intrathecal) | 8:1 | Yes |
| Clonidine HCl for Injection, 0.1 mg/mL (DURACLON) | 1:8 | Yes |
| Clonidine HCl for Injection, 0.1 mg/mL (DURACLON) | 8:1 | Yes |

Chemical Compatibility

The chemical compatibility of ziconotide with 5 other intrathecal drugs was determined by evaluating the ziconotide concentration while in admixture, by High Performance Liquid Chromatography (HPLC). The prepared admixtures were stored in polymethylpentene vials at 37° C. for a period of 60 days. Ziconotide diluted to 0.025 mg/ml with 0.9% Sodium Chloride for Injection, USP, was combined with each drug at a high and low concentration. The concentration of the other component in the admixture was not determined. Data from this study is presented below in Table 2.

TABLE 2

Chemical Compatibility

| Admixed Drug (Concentration) | Ziconotide Stability (Days above 90%) | Ziconotide Stability (Days above 80%) |
| --- | --- | --- |
| Hydromorphone HCl (2 mg/mL) | 32 days | 46 days |
| Hydromorphone HCl (10 mg/mL) | 3 days | 13 days |

TABLE 2-continued

Chemical Compatibility

| Admixed Drug (Concentration) | Ziconotide Stability (Days above 90%) | Ziconotide Stability (Days above 80%) |
|---|---|---|
| Morphine sulfate (5 mg/mL) | 13 days | 32 days |
| Morphine sulfate (25 mg/mL) | 3 days | 13 days |
| Fentanyl citrate (0.05 mg/mL) | 39 days | 60 days |
| Fentanyl citrate (0.10 mg/mL) | 39 days | 60 days |
| sufentanil citrate (0.01 mg/mL) | 60 days | 60 days |
| sufentanil citrate (0.05 mg/mL) | 60 days | 60 days |
| Clonidine HCl (0.5 mg/mL) | 60 days | 60 days |
| Clonidine HCl (3.0 mg/mL) | 60 days | 60 days |

Example 3

Compatibility of Ziconotide and INFUMORPH® (Morphine Sulfate) in the Medtronic SYNCHROMED® Infusion System The compatibility of ziconotide when mixed with morphine sulfate was determined by mixing 100 µg/ml of ziconotide with morphine sulfate (INFUMORPH®), and placing the admixture into a Medtronic SYNCHROMED® Infusion system (a drug dispensing implantable pump). Samples were obtained from the pump reservoir at specified intervals, and the concentrations of both drug components in the admixture were determined. Table 3 shows the stability of ziconotide, which is expressed as a percentage of the initial concentration of ziconotide.

TABLE 3

| Admixed Drug | Ziconotide: INFUMORPH ® Volume Ratio (final concentration) | Ziconotide Stability (Days above 90%) | Ziconotide Stability (Days above 80%) |
|---|---|---|---|
| INFUMORPH 200 (10 mg/mL) | 1:3 (25 µg/mL:7.5 mg/mL) | 7 days | 28 days |
| INFUMORPH 200 (10 mg/mL) | 1:9 (10 µg/mL:9 mg/mL) | 14 days | 28 days |
| INFUMORPH 500 (25 mg/mL) | 1:3 (25 µg/mL:22.5 mg/mL) | 0 days | 0 days |
| INFUMORPH 500 (25 mg/mL) | 1:9 (10 µg/mL:18.75 mg/mL) | 7 days | 14 days |

On average, the concentration of morphine sulfate remained above 90% of initial concentration in all admixtures for 60 days.

The pH of the admixtures remained within 1.0 pH unit of initial pH, ranging from 4.2 to 4.8. The appearance of the solutions did not change significantly, although a slight yellow color was observed in admixtures containing INFUMORPH® 500.

Example 4

Morphine and Ziconotide Interactions—Analgesic Activity of Concomitantly Administered Morphine and Ziconotide Synergistic Effect of Concomitantly Administered Morphine and Ziconotide (Hot-Plate and Tail Immersion Tests)

Continuous, intrathecal infusions of 0.03 µg/hr ziconotide produce, at most, modest increases in thermal (heat) response latencies in the rat hot-plate and tail immersion tests. However, when 0.03 µg/hr ziconotide is co-administered with moderately antinociceptive doses of morphine (15 µg/hr), response latencies in both tests greatly exceed those produced by either compound alone.

Additive Effect of Concomitantly Administered Morphine and Ziconotide (Formalin Test)

In the rat hindpaw formalin test, intrathecal bolus injections of a combination of ziconotide and morphine in a fixed dose ratio of 1:10, dose-dependently suppress formalin-induced tonic flinch responses. The measured $ED_{50}$ value is not significantly different from the value predicted by assuming additive analgesic effects. This observation suggests that morphine and ziconotide administered concomitantly in this model produce additive analgesic effects.

Our results show that intrathecal co-administration of ziconotide and morphine has a synergistic effect on analgesia in rat models of acute thermal nociception but has additive effects in a rat model of persistent pain (formalin test).

Tolerance to Ziconotide and/or Morphine

Studies in rats have shown that:

Ziconotide does not prevent the development of tolerance to the analgesic effects of morphine.

Ziconotide has no effect on morphine-induced analgesia in morphine-tolerant rats.

Subacute intrathecal infusion of ziconotide does not influence subsequent morphine analgesia.

The ability of ziconotide to affect the development of tolerance to the analgesic effects of morphine has been investigated using two rat models of acute pain: the hot plate test and the tail immersion test. The analgesic effects of morphine (15 µg/hr) administered by continuous intrathecal infusion declined in magnitude (i.e., tolerance develops) during subacute administration; after five days of a seven day morphine infusion, evoked pain behavior is comparable to that exhibited by saline-treated controls. Ziconotide (0.03 µg/hr) and morphine (15 µg/hr) administered in combination did not prevent this observed decline in the analgesic efficacy of morphine.

The ability of ziconotide to reverse morphine tolerance has been evaluated in the rat paw formalin test. Rats given intrathecal bolus injections of ziconotide (0.03 µg/hr) in combination with morphine (20 µg/hr) three hours after completion of seven days of continuous, constant-rate intrathecal morphine (15.18 µg/hr) infusions had post-formalin injection flinch counts equivalent to those observed in morphine-naive animals given ziconotide alone. These findings indicate:

1. Ziconotide does not restore the analgesic efficacy of morphine when it is administered to morphine-tolerant animals.

2. Rats tolerant to the analgesic effects of intrathecally-administered morphine do not exhibit cross-tolerance to ziconotide.

Subacute (six days) intrathecal infusion of ziconotide does not influence morphine-induced analgesia in the rat hindpaw formalin test (Omote, et al.). Intrathecal infusion of 0.005 µg/hr ziconotide for six days produced moderate, but not statistically significant, reductions in tonic formalin-induced flinching behavior. An intrathecal bolus injection of 1 µg morphine administered to animals pretreated for six days with intrathecal infusions of saline significantly reduced tonic flinch responses; the same dose of morphine produced slightly greater inhibition of tonic flinch behavior in rats that received intrathecal infusions of 0.005 µg/hr ziconotide for six days immediately preceding morphine treatment. These observations show that subacute intrathecal infusion of ziconotide does not reduce or prevent morphine-induced analgesia. In addition, these results are consistent with other findings indicating that acute intrathecal injection of ziconotide and morphine produces additive analgesic effects in the rat hindpaw formalin test.

Example 5

Behavioral and Cardiovascular Responses to Concomitantly Administered Morphine and Ziconotide Acute interactions between morphine administered subcutaneously (10 or 30 mg/kg) and ziconotide (0.1 μg) administered by intrathecal bolus injection were examined in rats using a conventional functional observational battery and measurements of heart rate and blood pressure. Gross behavioral and cardiovascular effects of SC morphine and intrathecal bolus injections of ziconotide were neither potentiated nor diminished when the compounds were administered concurrently. These findings indicate that analgesic doses of ziconotide are well tolerated when given intrathecal, either alone or in combination with high doses of SC morphine.

Example 6

Respiratory Effects of Concomitantly Administered Morphine and Ziconotide

Intrathecal administration of ziconotide did not depress respiratory minute volume responses to $CO_2$ inhalation in rats nor did it exacerbate acute respiratory depression induced by SC injections or morphine. Intrathecal bolus injection of ziconotide, at a dose (0.1 μg) that produces marked analgesia with minimal side effects did not depress respiratory minute volume responses to $CO_2$, nor did it exacerbate acute respiratory depression induced by SC bolus injection of morphine (10 or 30 mg/kg). Similarly, analgesic doses of ziconotide, administered subacutely by continuous intrathecal infusion (0.1 or 0.3 μg/hr), either alone or in combination with an analgesic dose of subcutaneously administered morphine (200 μg/hr), did not induce respiratory depression.

Ziconotide did not induce morphine-tolerant rats to become more sensitive to the respiratory depressant effects of morphine. Respiratory minute volume responses to $CO_2$ inhalation were comparable to control values when rats, made tolerant to the respiratory-depressant properties of morphine by SC injection of 10 mg/kg morphine twice daily for seven days, were given intrathecal injections of 0.1 μg ziconotide 30 minutes before a morphine challenge.

These findings confirm that ziconotide neither produces respiratory depression nor restores sensitivity to the respiratory-depressant properties of morphine when it is administered intrathecally to morphine-tolerant animals.

Example 7

Gastrointestinal Effects of Concomitantly Administered Morphine and Ziconotide

In rats, morphine administered by SC bolus injection produced a dose-dependent inhibition of GI transit. When morphine was administered in combination with an intrathecal dose of ziconotide (0.3 μg) that does not itself affect GI tract motility, the morphine does-response curve was shifted significantly to the left. This finding indicates that ziconotide and morphine interact synergistically to reduce GI transit in rats. In contrast, when mice were given a SC injection of morphine (3 mg/kg) together with an intrathecal dose of ziconotide (1 μg), gastrointestinal transit was reduced to an extent similar to that observed when morphine was administered alone. This finding does not conclusively exclude a potential interaction between the two compounds, because of the possibility that GI transit may have been maximally reduced by one or the other compound when administered alone.

Example 8

Analgesic Activity of Concomitantly Administered Baclofen and Ziconotide

Baclofen, a selective $GABA_B$ receptor agonist, is indicated for spinal use in the treatment of intractable spasticity caused by spinal cord injury or multiple sclerosis. Baclofen also possesses analgesic properties and is antinociceptive when administered by either parenteral or intrathecal routes in laboratory animals. In rats, intrathecal bolus injections of baclofen or ziconotide alone led to dose-dependent reductions in persistent pain behavior evoked by SC injection of 5% formalin into the dorsal hindpaw. When ziconotide and baclofen were administered in combination by intrathecal bolus injection, the effect on formalin-induced tonic pain behavior was statistically equivalent to the sum of the effects produced by each compound administered alone. These results indicate that concomitant intrathecal administration of ziconotide and baclofen produces additive analgesia in the rat hindpaw formalin test.

Example 9

Analgesic Activity of Concomitantly Administered Bupivacaine and Ziconotide

Bupivacaine is a sodium channel blocker that is used clinically both as a primary local anesthetic agent and as an adjuvant spinal analgesic. Intrathecal bolus injections of bupivacaine did not significantly inhibit formalin-induced acute or persistent hindpaw flinching behavior, however, 300 μg bupivacaine produced immediate but transient hindpaw paralysis. Intrathecal bolus injections of ziconotide (0.03, 0.1, or 0.3 μg) suppressed persistent pain behavior in a dose-dependent manner. When co-administered with ziconotide by intrathecal bolus injection, bupivacaine, administered in doses that did not produce complete nerve block, did not significantly alter ziconotide-induced analgesia. The results suggest that bupivacaine neither produces analgesia nor alters ziconotide-induced analgesia in the rat hindpaw formalin test.

Example 10

Analgesic Activity of Concomitantly Administered Clonidine and Ziconotide

Clonidine, an $\alpha_2$-adrenoceptor agonist, produces analgesia via centrally-mediated mechanisms when it is administered or systemically. Clonidine is used clinically to treat both acute (postoperative) pain and chronic pain syndromes. Intrathecal bolus injections of clonidine or ziconotide, administered alone or in combination, dose-dependently suppressed tonic pain behavior in the rat hindpaw formalin test. The theoretical additive $ED_{50}$ for the drug combination is not significantly different from the observed value nor is there a significant difference between the regression lines fitted to the log linear portions of the composite additive and mixture dose-response curves. These findings support the conclusion that ziconotide and clonidine have additive analgesic effects when concomitantly administered by the intrathecal route.

Example 11

Cardiovascular Responses of Concomitantly Administered Clonidine and Ziconotide Clonidine has known side effects of hypotension and bradycardia when used clinically for the management of pain. In rats, clonidine delivered by intrathecal bolus injection produced dose-dependent bradycardia and had dual effects on arterial blood pressure: low doses (1-3 μg) produced CNS-mediated hypotension, whereas high doses (10-50 μg) produced marked pressure responses due to the activation of peripheral $\alpha_2$-adrenoceptors in vascular smooth muscle. An intrathecal bolus injection of a high analgesic dose of ziconotide (0.3 μg), administered 10 minutes prior to clonidine injection, did not exacerbate the depressor or bradycardia responses elicited by intrathecal clonidine (3 μg) in conscious rats, indicating the absence of a significant drug interaction within the cardiovascular system.

Example 12

Continuous Intrathecal Infusion of Ziconotide in Rats and Dogs

The potential toxicity of ziconotide was evaluated by continuous intrathecal infusion for 28 days at doses in rats up to 1500 ng/kg/hr and in dogs up to 1200 ng/kg/hr; at least 30-fold the highest expected dose in patients.

Mean plasma drug levels measured in high-dose rats and dogs were approximately 3 and 10-fold greater than human, respectively, although overall systemic exposure to ziconotide was low (<4 ng/ml). Expected treatment-related pharmacological effects on the CNS, consisting mainly of tremors, shaking-behavior and/or ataxia, were of sufficient severity in dogs to require moribund euthanasia in 4/16 animals≥600 ng/kg/hour. There were no treatment-related changes in body weight, food intake or clinical pathology parameters nor was any target organ toxicity identified in either species at termination. Neurohistopathologic examinations revealed spinal cord compression with associated chronic inflammation in control and ziconotide-treated rats and dogs, which was attributed to pressure exerted by the IT catheter. This finding was not exacerbated with ziconotide exposure and no other histopathologic changes were observed. In conclusion, behavioral and neurological effects observed in rats and dogs receiving 28-day continuous IT infusions of ziconotide appeared related to the pharmacological activity of ziconotide with no associated neurotoxicity or histopathology. Further, no granuloma formation at the catheter tip was observed in ziconotide-treated dogs when infusion site tissue sections were examined, as has been reported with IT morphine administration (Yaksh, et al., Anesthesiology 2003; 99:174-87).

Example 13

Clinical Study of Combined Intrathecal Infusion of Ziconotide (Constant Dose) and Morphine (Increasing Dose)

Patient Criteria

The patient population included male and female patients on a stable dose of intrathecal (IT) ziconotide. The patients all had been on a dose of ziconotide of at least 0.2 μg/hr (4.8 μg/day). In addition, the patients either had sub-optimal pain relief demonstrated by a Visual Analog Scale of Pain Intensity (VASPI) score of ≥40 mm, or had residual pain not relieved by ziconotide and of a different nature than the pain relieved by ziconotide.

Ziconotide

Ziconotide was supplied at a concentration of 100 μg/mL in 5 mL single dose vials. The ziconotide dose was at least 0.2 μg/hr (4.8 μg/day). The mean dose of ziconotide during the 4-week treatment phase ranged from 26.5 μg/day at week 1 to 27.9 μg/day at week 4. The mean cumulative dose of ziconotide at termination was 731.1 μg. Patients were exposed to ziconotide for a mean duration of 27 days (range=3 to 30 days) during the 4-week combination treatment phase.

Morphine

Infumorph (preservative-free morphine sulfate sterile solution; Elkins Sinn, Inc., Cherry Hill, N.J.) was supplied in 20 mL glass ampules at a morphine concentration of either 10 or 25 mg/mL. The Infumorph dose escalation schedule was adjusted according to the individual patient's daily dose of systemic opiates. In the low dose regimen, patients receiving less than 100 mg/day oral morphine equivalents started at 0.25 mg/day and the dose was escalated to 0.5, 1.0, and 2.0 mg/day on weeks 2, 3, and 4, respectively. In the medium dose regimen, patients receiving 100-300 mg/day of oral morphine equivalents started at 0.5 mg/day, and the dose was escalated to 1.0, 2.0, and 3.0 mg/day on weeks 2, 3, and 4, respectively. In the high dose regimen, patients receiving over 300 mg/day of oral morphine equivalents started at a dose of 1.0 mg/day, and the dose was escalated to 2.0, 3.0, and 4.0 mg/day on weeks 2, 3, and 4, respectively. The dose escalation of Infumorph was stopped if intolerable adverse events occurred or significantly improved analgesia was obtained.

Patients were initiated on Infumorph in combination with IT ziconotide at the initial visit. Infumorph was initiated at a mean dose of 0.44 mg/day during week 1 of the study and increased weekly thereafter. Mean Infumorph doses were 0.80 mg/day, 1.41 mg/day, and 2.06 mg/day during weeks 2, 3, and 4 of treatment, respectively. The mean cumulative dose of Infumorph at termination was 31.1 mg (range: 1.3 to 71.0 mg). On average, patients were exposed to Infumorph for a total duration of 27 days (range: 3 to 30 days).

Efficacy Analysis

Efficacy measurements included the VASPI score, Categorical Pain Relief Scale (CPRS), Clinical Global Impression (CGI), and Weekly Systemic Opioid Consumption.

Statistical Efficacy Analysis

For the assessment of the efficacy of combined intrathecal ziconotide and morphine, patients rated their current pain intensity using the Visual Analog Scale of Pain Intensity (VASPI), Handbook of Pain Assessment (2nd Edition), D. C. Turk and R. Melzack, Eds, Guilford Press, New York, 2001. For the baseline evaluation, patients rated their current pain intensity on a 100-mm line representing the pain continuum (i.e., from "No Pain" to "Worst Possible Pain"). The left side of the continuum corresponds to a numerical score of 0 and the right side of the continuum corresponds to a numerical score of 100. At each study visit, the patient was asked to rate his/her current pain intensity using the same continuum described above. The primary pain efficacy evaluation for the trial was the percent change in VASPI while on combination therapy compared with the baseline measurement while on a single intrathecal analgesic (ziconotide).

Summary of Results

A total of 24 patients participated in the testing. Twenty-two (92%) patients completed the 4-week treatment phase and two (8%) patients discontinued treatment prematurely due to an adverse effect.

At the initial visit, VASPI scores ranged from 42 to 100 mm (n=24, mean=70.7 mm). All patients suffered from non-malignant pain, which was classified as neuropathic (n=20, 83%), nociceptive (n=10, 42%) or degenerative (n=9, 38%). Patients had suffered with pain for an average duration of 14.8 years, ranging from 4 to 40 years. All patients were refractory to pain treatment (n=24, 100%). In addition, ten patients (42%) had failed back surgery syndrome.

Figure 1:
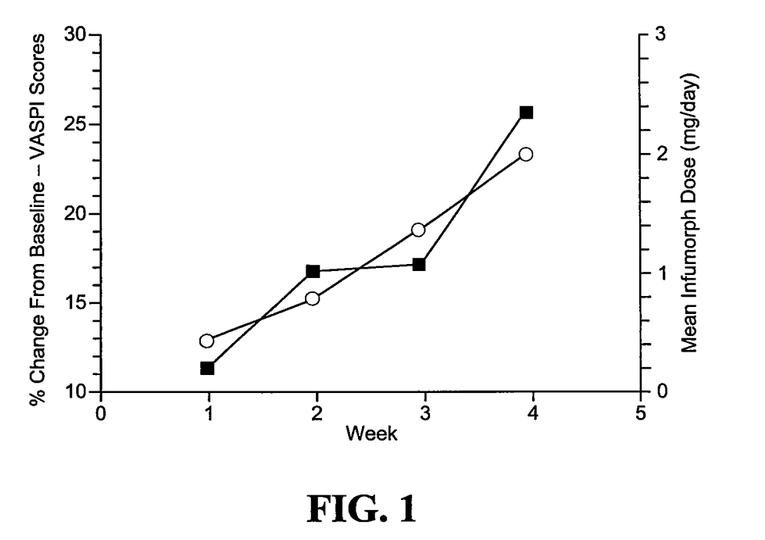
FIG. 1 shows (a) the mean percent change from baseline in VASPI scores (■), and (b) mean Infumorph dose (○) for each week throughout the 4-week combination treatment phase.

The primary efficacy measure (VASPI) was assessed weekly throughout the 4-week combination treatment phase. FIG. 1 shows (a) the mean percent change from baseline in VASPI scores (■), and (b) mean Infumorph dose (○) for each week throughout the 4-week combination treatment phase. On average, a reduction in pain intensity was observed at each week. Weekly VASPI reductions corresponded with increased Infumorph doses throughout the 4-week treatment phase. The mean percent reduction in VASPI scores was 11.3% after one week of combination therapy and 26.1% after four weeks of combination therapy when compared with baseline measurement on a single ziconotide treatment.

Example 14

Clinical Study of Combined Intrathecal Infusion of Morphine (Constant Dose) and Ziconotide (Increasing Dose)

Patient Criteria

The patient population included male and female patients on a dose of IT morphine ranging between 2 and 20 mg/day. Patients either had sub-optimal pain relief demonstrated by a Visual Analog Scale of Pain Intensity (VASPI) score of ≥40 mm, or had residual pain not relieved by morphine and of a different nature than the pain relieved by morphine (e.g., neuropathic pain).

Ziconotide

Ziconotide was supplied at a concentration of 100 μg/mL in 5 mL single dose vials. Ziconotide doses increased weekly throughout the treatment phase of the study, starting at 0.025 μg/hour (0.6 μg/day) at baseline. Patients were seen weekly thereafter and received increased ziconotide dose as follows: 0.05 μg/hr (1.2 μg/day) at Visit 2 (Day 7), 0.10 μg/hr (2.4 μg/day) at Visit 3 (Day 14), 0.20 μg/hr (4.8 μg/day) at Visit 4 (Day 21), and 0.30 μg/hr (7.2 μg/day) at Visit 5 (Day 28). The dose escalation of ziconotide was stopped if intolerable adverse events occurred, significantly improved analgesia was obtained, or if the final dose of 0.30 μg/hr was reached. The mean cumulative dose of ziconotide at termination was 74.4 μg (range: 8.8 to 118.6 μg), and the mean dose during week 5 was 0.197 μg/mL. On average, patients were exposed to ziconotide for a total duration of 31.5 days (range: 14 to 35 days).

Morphine

Infumorph (preservative-free morphine sulfate sterile solution; Elkins Sinn, Inc., Cherry Hill, N.J.) was supplied in 20 mL glass ampoules at a morphine concentration of either 10 or 25 mg/mL. The Infumorph dose remained stable throughout the combination treatment phase of the study and ranged between 2 and 20 mg/day.

All patients (n=22) were receiving IT Infumorph therapy at the screening visit at a mean dose of 12.3 mg/day (range: 2.0 to 20.0 mg/day). Subsequently, patients were stabilized on IT Infumorph monotherapy at a mean dose of 12.4 mg/day (range: 1.8 to 20.0 mg/day) for an average duration of 8.8 days prior to receiving combination IT Infumorph and ziconotide therapy at the baseline visit. The mean dose of Infumorph during the 5-week treatment phase ranged from 12.4 mg/day at week 1 to 12.7 mg/day at week 5. Patients were exposed to Infumorph for a mean duration of 40.7 days (range=25 to 56 days) during the screening and 5-week combination treatment phases.

Efficacy Analysis

Efficacy measurements included the VASPI score, Categorical Pain Relief Scale (CPRS), Clinical Global Impression (CGI), and Weekly Systemic Opioid Consumption.

Statistical Efficacy Analysis

For the assessment of the efficacy of combined intrathecal ziconotide and morphine, patients rated their current pain intensity using the Visual Analog Scale of Pain Intensity (VASPI), as described in Example 13. The primary pain efficacy evaluation for the trial was the percent change in VASPI while on combination therapy compared with the baseline measurement while on a single intrathecal analgesic (morphine).

Summary of Results

A total of 22 patients participated in the testing. Sixteen (73%) patients completed the 5-week treatment phase and six (27%) patients discontinued treatment prematurely due to an adverse effect.

At screening, VASPI scores ranged from 41 to 91 mm (mean=66.6 mm). On average, pain intensity increased from the screening visit to the baseline visit (mean=71.7 mm). All patients suffered from non-malignant pain, which was classified as neuropathic (n=16, 73%) or mixed (n=13, 59%). Patients had suffered with pain for an average duration of 9.6 years, ranging from 2.5 to 40 years. In addition, the majority of patients (n=20, 91%) had failed back surgery syndrome and were refractory to pain treatment.

Figure 2:
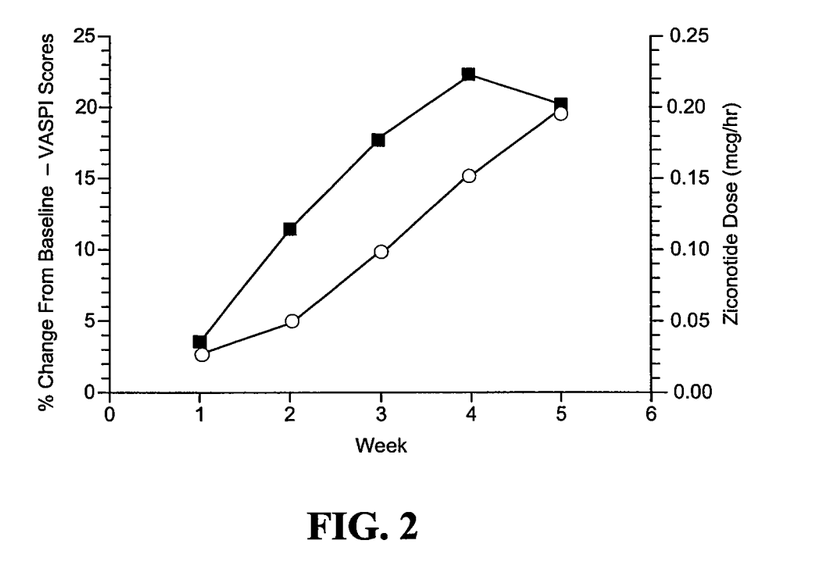
FIG. 2 shows (a) the mean percent change from baseline in VASPI scores (■), and (b) mean ziconotide dose (○) for each week throughout the 5-week combination treatment phase.

The primary efficacy measure (VASPI) was assessed weekly throughout the 5-week combination treatment phase. FIG. 2 shows (a) the mean percent change from baseline in VASPI scores (■), and (b) mean ziconotide dose (○) for each week throughout the 5-week combination treatment phase. On average, a reduction in pain intensity was observed at each week through week 5. Weekly VASPI reductions corresponded with increased ziconotide doses throughout the 5-week combination phase with the exception of the final dose increase at week 5 (see FIG. 2). The mean percent reduction in VASPI scores was 2.7% after one week of combination therapy and 21.4% after 5 weeks of combination therapy.

Example 15

Clinical Study Protocol of Combined Intrathecal Infusion of Baclofen (Constant Dose) and Ziconotide (Increasing Dose)

Patient Criteria

The patient population includes male and female patients on a dose of IT baclofen (either compounded baclofen or LIORESAL®) ranging between 22 and 800 μg/day. Patient has pain and sub optimal pain relief indicated by a minimum VASPI of 40 mm at the Screening and Baseline Visit.

Visit 1/Baseline Visit (Day 0)

All patients must be on stable doses of LIORESAL® (between 22 and 800 μg/d), systemic opioids, and other concomitant medications for at least 7 days prior to the Baseline Visit. The contents of the SynchroMed® EL Infusion System are removed and replaced with PRIALT™ and LIORESAL®. The LIORESAL® dose remains the same as during the last 7 days of the screening period and throughout the first 9 weeks of the trial. The initial dose of PRIALT™ is 0.025 µg/hr (0.6 µg/d).

PRIALT™

The initial PRIALT™ dose is 0.025 µg/hr (0.6 µg/d) for one week starting at Baseline (Day 0). After one week of treatment, the pump is refilled and the dose increased to 0.05 µg/hr (1.2 µg/d). After the third week of treatment, the pump is refilled and the dose increased to 0.10 µg/hr (2.4 µg/d). After five weeks of treatment, the pump is refilled and the dose increased to 0.15 µg/hr (3.6 µg/d). After seven weeks of treatment, the pump is refilled and the dose increased to 0.20 µg/hr (4.8 µg/d). During the final week, the dose will be maintained at 0.20 µg/hr (4.8 µg/d). Dose increases are made until an Escalation Stopping Criterion is encountered.

LIORESAL®

The LIORESAL® dose is kept constant and unchanged from the stable dose established during screening and is at least 22 µg/day and no more than 800 µg/day.

Pump Flow Rate

The pump flow rate is held constant and is at least 12 mcl/hr (288 mcl/d) to allow for clearance of the pump volume within one or two days. Drug dosage is not to be adjusted by changing the pump flow rate as this would change the rate of infusion of both compounds.

Pain Measurement

Visual Analog Scale of Pain Intensity (VASPI) is determined at each clinic visit. Categorical Pain Relief Scale (CPRS) is determined at Visit 7/Early Termination and Extension Phase Termination Visit if applicable. Clinical Global Impression (CGI) is determined at Visit 7/Early Termination and Extension Phase Termination Visit if applicable.

Other Clinical Measurements

Spasticity scales (Modified Ashworth Scale: 0-4 normal to rigid tone; Spasm Scale 0-4 no spasms to greater than 10 per hr; Penn Spasm Frequency Scale, Visual Analogue of Spasticity Scale or VASS) is determined at each clinic visit.

Efficacy Variables

Primary Efficacy Variable includes: Percentage change in VASPI scores from the Baseline Visit to Visit 7/Early Termination Visit.

Secondary Efficacy Variables include:

Percentage change in VASS scores from the Baseline Visit to Visit 7/Early Termination Visit.

Change in VASPI and VASS scores from the Baseline Visit to Visit 7/Early Termination.

Percentage change and change in VASPI and VASS scores from the Baseline Visit to each of Visits 2-6.

Distribution of CPRS at Visit 7/Early Termination Visit.

Distribution of CGI at Visit 7/Early Termination Visit.

Change and percent change in weekly systemic opiate consumption.

Change and percent change in weekly oral baclofen consumption.

Spasticity scale changes.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method for treating severe chronic pain in a human patient, comprising:
   (a) administering to a human patient suffering from severe chronic pain who has an implantable pump a therapeutically effective amount of an ω-conopeptide by continuous intrathecal infusion using the pump, and
   (b) administering to the human patient a therapeutically effective amount of an opioid without admixing the ω-conopeptide and the opioid in the pump, wherein the opioid is morphine or hydromorphone.

2. The method of claim 1, wherein the opioid is morphine.

3. The method of claim 1, wherein the ω-conopeptide is ziconotide.

4. The method according to claim 3, wherein said ziconotide is administered in a pharmaceutical composition comprising an antioxidant.

5. The method according to claim 4, wherein said antioxidant is methionine.

6. The method according to claim 4, wherein said pharmaceutical formulation has pH between 4 and 4.5.

7. A method for treating severe chronic pain in a human patient, comprising:
   (a) administering to a human patient suffering from severe chronic pain who has an implantable pump a therapeutically effective amount of an ω-conopeptide by continuous intrathecal infusion using the pump, and
   (b) administering to the human patient a therapeutically effective amount of an opioid, wherein the opioid is morphine or hydromorphone, and
   (c) recommending against admixing the ω-conopeptide with the opioid for a period longer than a week.

8. The method according to claim 7, wherein the period is longer than 14 days.

9. The method according to claim 8, wherein the opioid is hydromorphone.

10. The method according to claim 8, wherein the opioid is morphine.

11. The method of claim 8, wherein the ω-conopeptide is ziconotide.

12. The method according to claim 11, wherein said ziconotide is administered in a pharmaceutical composition comprising an antioxidant.

13. The method according to claim 12, wherein said antioxidant is methionine.

14. The method according to claim 12, wherein said pharmaceutical formulation has pH between 4 and 4.5.

15. A method for treating severe chronic pain in a human patient, comprising the steps of:
   (a) selecting a human patient suffering from severe chronic pain who is being administered a therapeutically effective amount of an ω-conopeptide by continuous intrathecal infusion with an implantable pump, the human patient is also being administered a therapeutically effective amount of an opioid, wherein the opioid is morphine or hydromorphone, and
   (b) recommending against admixing the ω-conopeptide and the opioid in the pump.

16. The method of claim 15, wherein the opioid is morphine.

17. The method of claim 15, wherein the ω-conopeptide is ziconotide.

18. A method for treating severe chronic pain in a human patient that is suffering from severe chronic pain and who has an implantable pump which administers a therapeutically effective amount of an ω-conopeptide by continuous intrathecal infusion, the method comprises the step of:

administering to the human patient a therapeutically effective amount of an opioid, recommending against admixing the ω-conopeptide and the opioid in the pump, wherein the opioid is morphine or hydromorphone.

19. The method of claim 18, wherein the opioid is morphine.

20. The method of claim 18, wherein the ω-conopeptide is ziconotide.

21. The method of claim 18, wherein the opioid is orally or parenterally administered to the human patient.

22. The method of claim 18, wherein the ω-conopeptide is formulated with an anti-oxidant in a pharmaceutical composition.

23. The method of claim 18, wherein the ω-conopeptide is administered after the onset of pain.

24. The method of claim 18, wherein the ω-conopeptide is administered before an event known to elicit a severe chronic pain.

* * * * *